(12) United States Patent
Borck

(10) Patent No.: US 8,450,455 B2
(45) Date of Patent: May 28, 2013

(54) CRGD PEPTIDE DERIVATIVE AND ITS MANUFACTURE, AND IMPLANT HAVING A COATING CONTAINING A CRGD PEPTIDE DERIVATIVE

(75) Inventor: Alexander Borck, Aurachtal (DE)

(73) Assignee: Biotronik AG, Buelach (CH)

( * ) Notice: Subject to any disclaimer, the term of this patent is extended or adjusted under 35 U.S.C. 154(b) by 0 days.

(21) Appl. No.: 13/291,888

(22) Filed: Nov. 8, 2011

(65) Prior Publication Data

US 2012/0121682 A1    May 17, 2012

Related U.S. Application Data

(60) Provisional application No. 61/412,798, filed on Nov. 12, 2010.

(51) Int. Cl.
*A61K 38/12* (2006.01)
*A61P 19/10* (2006.01)

(52) U.S. Cl.
USPC .......................................... 530/317; 424/423

(58) Field of Classification Search
None
See application file for complete search history.

(56) References Cited

FOREIGN PATENT DOCUMENTS

WO   WO 2007/146001   12/2007
WO   WO 2010/002584   1/2010

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-497.*
Bradley et al., Limits of Cooperativity in a Structurally Modular Protein: Response of the Notch Ankyrin Domain to Analogous Alanine Substitut~ons in Each Repeat, J. Mol. BIoL (2002) 324, 373-386.*
Definition of derivative, from on-line medical dictionary (http://cancerweb.ncl.ac.uk/cgi-bin/omd?query=derivative), pp. 1-5. Accessed Jul. 7, 2005.*
Zhang et al, Effects of immobilizing sites of RGD peptides in amphiphilic block copolymers on efficacy of cell adhesion, Biomaterials, 2010, 31, pp. 7873-7882.*
Isernia et al, Synthesis and conformation of dipeptide taste ligands containing homo-beta-amino acid residues, Journal of Physical Organic Chemistry, 1999, 12, pp. 577-587.*
Rodriguez et al, Synthesis of Gastrin Antagonists, Analogues of the C-Terminal Tetrapeptide of Gastrin, by Introduction of a beta-Homo Residue, J. Med. Chem., 1989, 32, pp. 522-528.*

Zhan C et al., "Cyclic RGD conjugated poly(ethylene glycol)-co-poly(lactic acid) micelle enhances paclitaxel anti-glioblastoma effect," Journal of Controlled Release, Elsevier, Amsterdam, NL. Bd. 143, Nr. 1, 2. Apr. 2010.
Kim et al., "Self-assembled glycol chitosan nanoparticles for the sustained and prolonged delivery of antiangiogenic small peptide drugs in cancer therapy," Biomaterials, Elsevier Science Publishers, BV., Barking, GB., Bd, 29, Nr. 12, 4. Mar. 2008.
NG Jeck Fei et al., "Cationized bovine serum albumin with pendant RGD groups forms efficient biocoatings for cell adhesion." Journal of Biomedical Materials Research. Part B, Applied Biomaterials Nov. 2011.
Norased Nasangkla et a., "cRGD-Functionalized Polymer Micelles for Targeted Doxorubicin Delivery," Angewandte Chemic, Int. Ed. 2004, 43. pp. 6323-6327. Jan. 2004.

* cited by examiner

*Primary Examiner* — Julie Ha
*Assistant Examiner* — Li Ni Komatsu
(74) *Attorney, Agent, or Firm* — Greer, Burns & Crain, Ltd.

(57) ABSTRACT

Various embodiments of the invention relate to a cRGD peptide derivative and an associated manufacturing method, and to an implant having a coating containing a cRGD peptide derivative. One aspect of the invention is the provision of a cRGD peptide derivative having the formula (1):

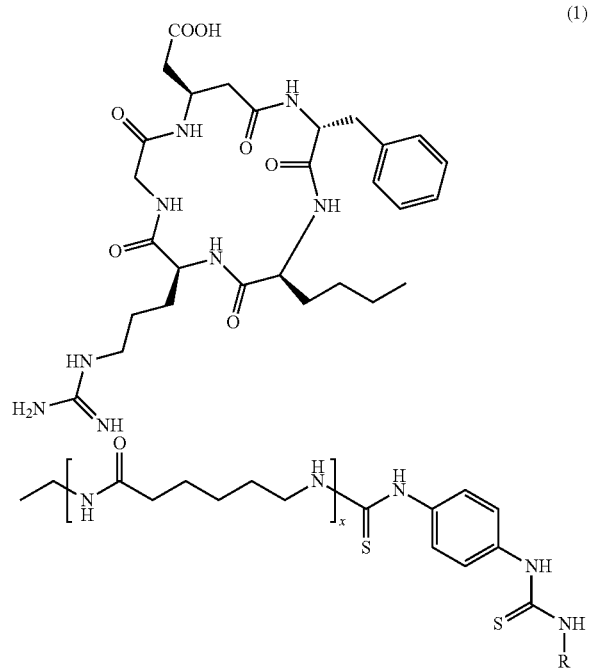

(1)

wherein x=0-8, in particular 4-8, and R is a hydrophobic group.

19 Claims, No Drawings

CRGD PEPTIDE DERIVATIVE AND ITS MANUFACTURE, AND IMPLANT HAVING A COATING CONTAINING A CRGD PEPTIDE DERIVATIVE

RELATED APPLICATION

This patent application claims the benefit of U.S. Provisional Patent Application No. 61/412,798, filed on Nov. 12, 2010, which is hereby incorporated by reference in its entirety.

TECHNICAL FIELD

Some embodiments of the invention relate to a cRGD peptide derivative, a method of manufacture, and an implant having a coating containing the cRGD peptide derivative.

BACKGROUND

Implants are utilized in modern medical technology in a variety of applications. They are used e.g. to support vessels, hollow organs, and ductal systems (endovascular implants e.g. stents), to fasten and temporarily fix tissue implants and tissue transplants in position, as well as for orthopedic purposes such as pin, plate, or screw. The stent is a form of an implant that is used particularly frequently.

Stent implantation has been established as one of the most effective therapeutic measures for treating vascular disease. Stents may be used to provide support in a patient's hollow organs. To this end, some stents have a filigree support structure composed of metallic struts that are initially present in a compressed form for insertion into the body, and are expanded at the application site. One of the main applications of stents of this type is to permanently or temporarily widen and hold open vasoconstrictions, including constrictions (stenoses) of the coronary arteries. In addition, aneurysm stents are known, for example, which are used to support damaged vascular walls.

Some stents include a circumferential wall, providing support that suffices to hold the constricted vessel open to a desired extent, and a tubular base body through which blood continues to flow without restriction. The circumferential wall can be formed by a latticed support structure that enables the stent to be inserted in a compressed state, having a small outer diameter, until it reaches the constriction in the particular vessel to be treated, and to be expanded there, e.g. using a balloon catheter, to the extent that the vessel has the desired, increased inner diameter.

An implant, for example a stent, has a base body composed of an implant material. An implant material is a nonliving material that is used for a medical application and interacts with biological systems. A prerequisite for the use of a material as an implant material that comes in contact with the body environment when used as intended is its biocompatibility. "Biocompatibility" refers to the capability of a material to evoke an appropriate tissue response in a specific application. This includes an adaptation of the chemical, physical, biological, and morphological surface properties of an implant to the recipient tissue, with the objective of achieving a clinically desired interaction. The biocompatibility of the implant material may also be dependent on the time sequence of the response of the biosystem in which the implant is placed. For example, irritations and inflammations, which can cause tissue changes, occur over the relative short term. Biological systems therefore respond differently depending on the properties of the implant material. Depending on the response of the biosystem, implant materials can be subdivided into bioactive, bioinert, and degradable/resorbable materials.

Implant materials include polymers, metallic materials, and ceramic materials (as coating, for example). Biocompatible metals and metal alloys for permanent implants contain e.g. stainless steels (e.g. 316L), cobalt-based alloys (e.g. CoCrMo casting alloys, CoCrMo forging alloys, CoCrWNi forging alloys, and CoCrNiMo forging alloys), pure titanium and titanium alloys (e.g. CP titanium, TiAl6V4 or TiAl6Nb7), and gold alloys. In the field of biocorrodible stents, the use of magnesium or pure iron and biocorrodible base alloys of the elements magnesium, iron, zinc, molybdenum, and tungsten is proposed.

A biological response to polymeric, ceramic, or metallic implant materials depends on the concentration, duration of exposure, and type of supply. The presence of an implant material may evoke inflammatory responses which can be triggered by mechanical irritations, chemical substances, or metabolites. The inflammatory process is typically accompanied by the immigration of neutrophil granulocytes and monocytes through the vascular walls, the immigration of lymphocyte effector cells with the formation of specific antibodies to the inflammatory stimulus, activation of the complement system with the release of complement factors which act as mediators, and, ultimately, activation of blood coagulation. An immunological response is usually closely associated with the inflammatory response and can lead to sensitization and the development of allergies. Known metallic allergens include e.g. nickel, chromium, and cobalt which are also used in many surgical implants as alloying constituents. A main problem associated with the implantation of a stent in a blood vessel is in-stent restenosis due to excessive neointimal growth caused by a strong proliferation of arterial smooth muscle cells and a chronic inflammatory response.

A greater level of biocompatibility can be achieved by coating implant materials with particularly tissue-compatible materials. These materials are usually organic or synthetic polymeric in nature and are partially of natural origin. Further strategies for preventing restenosis focus on inhibiting proliferation using medication, for example, treatment using cytostatic agents. The active ingredients can be provided on the implant surface in the form of a coating.

The RGD triad (Arg-Gly-Asp) serves many integrins as a primary recognition site for proteins of the extracellular matrix. Peptides that contain this sequence can therefore mimic the ligands of these integrins and bind thereto. Linear RGD peptides display a low affinity to many integrins, but a head-to-tail cyclization of pentapeptides results in a conformational constriction, thereby increasing the capability to bind to some integrins. Peptides that bind selectively to certain integrins or integrin groups and therefore inhibit them can be synthesized by selecting the amino acids that flank the RGD sequence such that this objective is met. Due to the fact that RGD peptides are selective antagonists for integrins, their medical relevance—or the medical relevance of peptidomimetics derived therefrom—is the subject of research. For example, the integrin $\alpha_v\beta_3$, which is expressed by tumor cells very frequently and plays a key role in the mechanism of invasive tumor growth, is well-inhibited by the peptide c(RGDfV). Furthermore, cRGD peptides are used as inhibitors for angiogenesis in tumor diseases, and in osteoporosis.

In terms of developing implants coated with active ingredients, in particular stents coated with active ingredients (which are referred to as DES stents), the use of cRGDs is a proposed approach to improving the compatibility of implants. Mainly, however, cRGDs can be used to improve the healing process. To achieve a long-term antiproliferative effect, however, it is usually necessary to release other active ingredients, for example, rapamycin, from the coating. Adding cRGD subsequently to an existing coating system therefore creates the problem of ensuring that cRGDs are provided on the surface of the implant at the earliest possible point in time, while ensuring that the elution characteristic of an active ingredient contained in a base of the coating underneath the surface does not change. Otherwise, the elution characteristic of the active ingredient would have to be re-optimized, which is very difficult to do in isolated cases, and which makes it difficult to vary the system.

SUMMARY

This and other problems of conventional coated implants are addressed by the present cRGD derivative on a surface of an implant. Advantageously, provision of cRGDs on the surface of the implant is such that the elution characteristic of the base layer situated underneath does not change, or changes only unsubstantially, for an active ingredient embedded in the base layer. Furthermore, in at least some embodiments the recognition sites of the cRGDs are accessible immediately after implantation, instead of their becoming exposed by the gradual degradation of the coating matrix.

In one embodiment, a cRGD peptide derivative is provided having the formula (1):

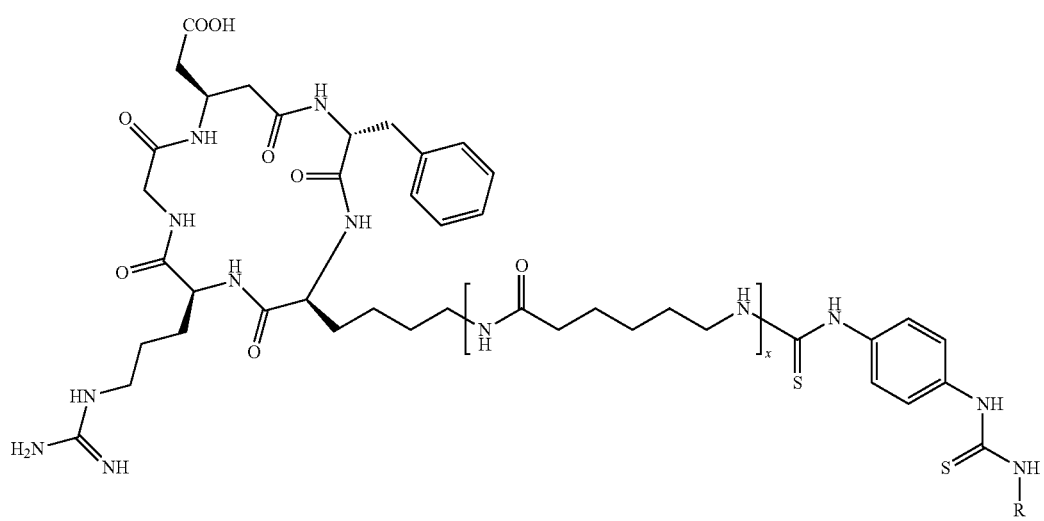

(1)

wherein x=0-8 and R is a hydrophobic group.

In another embodiment, an implant including a coating that contains the cRGD peptide derivative of formula (1) is provided.

Yet another aspect of this invention is a method of manufacturing the cRGD peptide derivative of formula (1), which includes the step of covalent coupling of a primary amine having the formula R—NH2 with the isothiocyanate group of a cRGD peptide derivative having the formula (2):

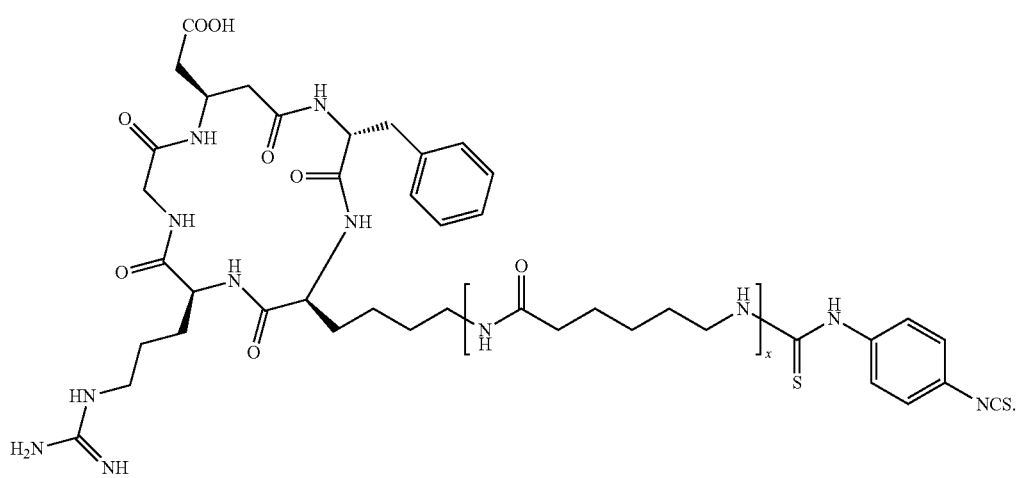

(2)

DETAILED DESCRIPTION

In one embodiment, a cRGD peptide derivative is provided having the formula (1):

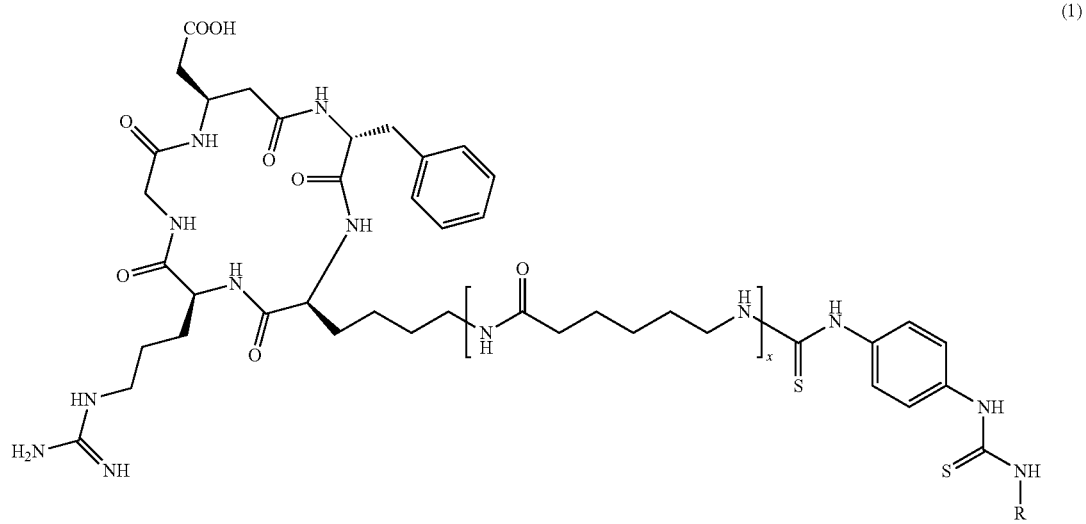

(1)

wherein x=0-8, in particular 4-8, and R is a hydrophobic group.

At least some embodiments are based on the finding that, due to the hydrophobic group R, the cRGD peptide can form a monolayer, by self-assembly, on the hydrophobic base of an implant coating. Thus, the hydrophobic domain of the peptide extends into the hydrophobic base of the coating, thereby directing the recognition sides of the cRGDs outwardly.

As is known in the art, a P value, or the octanol-water partition coefficient, is a dimensionless partition coefficient that represents a ratio of concentrations of a chemical in a two-phase system composed of 1-octanol and water (at 25° C.). P is typically presented in the form of the common logarithm as log P. Hydrophobic group R is preferably created such that a primary amine R—$NH_2$ having the same "R" group, has a log P value greater than −0.2, and in some embodiments greater than 1.9.

Some aspects of the invention are based on the discovery that, due to the hydrophobic group, a cRGD peptide, having a hydrophobic domain defined by the region containing the group R and a recognition domain defined by a region opposing the hydrophobic domain, is designed to form a monolayer, by self-assembly, on the hydrophobic base of an implant coating. The hydrophobic domain of the present peptide extends into the hydrophobic base of the coating, thereby directing the recognition sides of the cRGDs outwardly. Advantageously, the present cRGDs are designed to be provided on the surface of the implant such that the elution characteristic of the base layer situated underneath does not change, or changes only unsubstantially, for an active ingredient embedded in the base layer. Furthermore, an improvement over the state of the art is provided in that the recognition sites of the cRGDs are accessible immediately after implantation, instead of their becoming exposed by gradual degradation of the coating matrix.

Furthermore, in some embodiments, R is selected from the group that includes substituted or unsubstituted aliphatic hydrocarbons (e.g. an alkyl residue such as heptyl, or a halogenated alkyl residue); substituted or unsubstituted heteroaliphatic hydrocarbons having at least one heteroatom selected from N, O, S or P; substituted or unsubstituted aromatics (e.g. a 2-anthracyl residue or a 4-heptylaryl residue); and substituted or unsubstituted N-, O-, S- or P-heteroaromatics.

In other embodiments, R stands for a polymeric group selected from chitosan, polylysine (e.g., poly-D-lysine), poly (lactide-co-glycolide) (PLGA), and polylactide (PLA).

A further aspect of some embodiments of the invention is the provision of an implant, such as a stent, having a coating that contains the cRGD peptide derivative named above. The coating includes (i) a base composed of a hydrophobic material that optionally contains an active ingredient; and (ii) a cover layer that contains the present cRGD peptide derivative or is composed thereof.

In another embodiment of a coated implant, the hydrophobic material of the base contains poly(lactide-co-glycolide) (PLGA) or polylactide (PLA), and the cRGD peptide derivative in the cover layer contains a hydrophobic polymeric group composed of poly(lactide-co-glycolide) (PLGA) or polylactide (PLA). The molecular weight of the polymeric group is optionally specified in terms of the material of the base of the implant coating, that is, in some embodiments the material of the base and the functionalized cRGD are matched to each other and both contain, for example, polylactide fragments having the same chain length.

Thus, this aspect of some invention embodiments is based on the discovery, among others, that a thin cover layer can be formed on a base at least partially (and optionally entirely) composed of a hydrophobic material that optionally contains an active ingredient, in a particularly simple manner using the cRGD peptide derivatives according to the invention. The cover layer may be (but is not necessarily) present as a monolayer, in the case of which the hydrophobic group of the cRGD peptide derivative extends into the hydrophobic base material. As a result, the elution characteristic of the base for the active ingredient is not changed, or it is merely changed to a very small extent.

In these embodiments, the implant therefore includes a coating composed of at least two components, a base layer that is applied to the base body and is composed of a hydrophobic material, and a cover layer that covers this base layer at least partially (and in some embodiments completely), the cover layer in some embodiments being entirely composed of the cRGD peptide derivative, and in other embodiments containing the cRGD peptide derivative with other materials.

A further aspect of the invention is the provision of another embodiment including a method for manufacturing the above-mentioned cRGD peptide derivative having the formula (1). The method comprises the step: covalent coupling of a primary amine having the formula R—$NH_2$ with the isothiocyanate group of a cRGD peptide derivative having the formula (2)

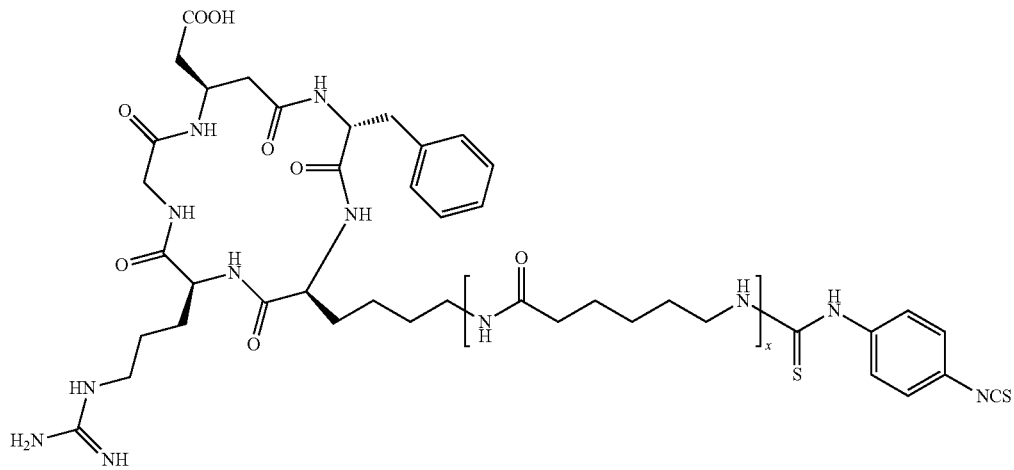

(2)

According to the invention, a coating refers to the application, at least in sections, of the components of the coating on the base body of the implant. Preferably, the coating covers the entire surface of the base body of the implant. A layer thickness is preferably in the range of 1 nm to 100 μm, and particularly preferably 300 nm to 15 μm, although other thicknesses will prove to be useful. The coating can be applied directly to the surface of the implant. The processing can be performed using standard methods for the coating including spraying, dipping, deposition, and others. The base layer can be composed of single-layered systems or multiple-layered systems (e.g. base coat layers, drug coat layers, or top coat layers). The base layer can be applied directly to the base body of the implant, or further layers can be provided therebetween. Methods for coating implants, for creating the base layer, and for creating the cover layer are known to a person skilled in the art and for sake of brevity need not be discussed in detail herein.

According to the invention, an active ingredient is a medicinal agent having a pharmaceutical effect, and which is used in the human body or animal body to cure, alleviate, prevent, or detect illness. Active ingredients include paclitaxel, sirolimus, rapamycin (and rapamycin derivatives). Some useful active ingredients act via the mTOR recognition site. Other active ingredients include, RAS inhibitors, including those that prevent RAS adhesion. Other active ingredients will be apparent to those knowledgeable in the art.

In another embodiment, the cover layer is composed of one or more of chitosan or polylysine. Chitosan or polylysine can be applied in a diluted aqueous solution, e.g. to a stent that may have also been precoated with a base material containing an active ingredient, using a spraying process or an immersion process. Subsequent coupling with cRGDs takes place in the aqueous medium; when lipophilic active ingredients are used, there is no risk that the active ingredients bound in the base will elute in this medium and thereby lower the load of active ingredient.

The compound having the formula (2) is known (*Jörg Auernheimer; Funktionalisierung künstlicher Oberflächen mit Integrinliganden zur Stimulierung integrinvermittelter Zelladhäsion; dissertation; TU München;* 2005; chapter 6.4; page 136). Examples of primary amines that are suitable for coupling are 2-aminoanthracene, 4-heptylaniline, or 1-aminoheptane, which bind to the reactive group without secondary reactions.

Various aspects of the invention are explained below in greater detail with reference to example embodiments.

Reaction of the Compound Having the Formula (2) with 1-Aminoheptane

React 2 ml of the compound having the formula (2) with x=4 in a concentration of 5 mg/ml in phosphate buffered saline ("PBS") at room temperature with 1.52 mg 1-aminoheptane (logP 2.57). The solution obtained in this manner can be sprayed onto a surface, which contains an active ingredient, of an implant composed of a base body and a matrix that contains an active ingredient. After drying, the amino acid units are on the surface, while the lipophilic group interacts with the layer that contains the active ingredient. The bond strength is increased with a more lipophilic matrix-bound active ingredient and a more lipophilic matrix.

The stability of the bond can be further increased as follows:

Place the stents that have a layer containing an active ingredient, and that have a cRGD cover layer, in a chloroform atmosphere for 30 minutes. Under this solvent influence, the PLLA surface is partially dissolved, and therefore the heptane group is inserted into the outer surface. The cRGDs immobilized in this manner are captively bound.

Reaction of the Compound Having the Formula (2) on PLLA Surface

Cover 10 ml chloroform with a layer of 2 ml water. Add the cRGDs (x=4) in 500 μl aqueous solution (concentration: 5 mg/ml).

Immerse the stent, which is coated with polylactide (PLLA), into the chloroform phase and incubate for 1-5 seconds at RT. As the stent is slowly removed, the cRGDs and their lipophilic group attach to the swollen PLLA. After drying, the cRGDs are captively bound. The peptides are expressed and can interact with integrins.

Reaction of the Compound Having the Formula (2) on Chitosan Surface

Spray a stent comprising a coating of PLLA and sirolimus with a solution of chitosan in diluted acetic acid (0.3%). After drying, immerse the stent in a buffered (phosphate buffer 50 mM) aqueous solution of a cRGD having the formula (2) with x=4 (concentration: 5 mg/ml; pH 7; room temperature). After 1 hour, all amine groups of the chitosan have reacted with the thiocyanate groups of the cRGD.

The stent does not exhibit deviating elution kinetics for sirolimus. In contrast to stents that have been coated solely with PLLA and sirolimus, a first endothelial covering is visible just three days after implantation.

It will be apparent to those skilled in the art that numerous modifications and variations of the described examples and embodiments are possible in light of the above teaching. The disclosed examples and embodiments are presented for purposes of illustration only.

Therefore, it is the intent to cover all such modifications and alternate embodiments as may come within the true scope of this invention.

What is claimed is:

1. A cyclic Arginine-Glycine-Aspartate (cRGD) peptide derivative having the formula (1):

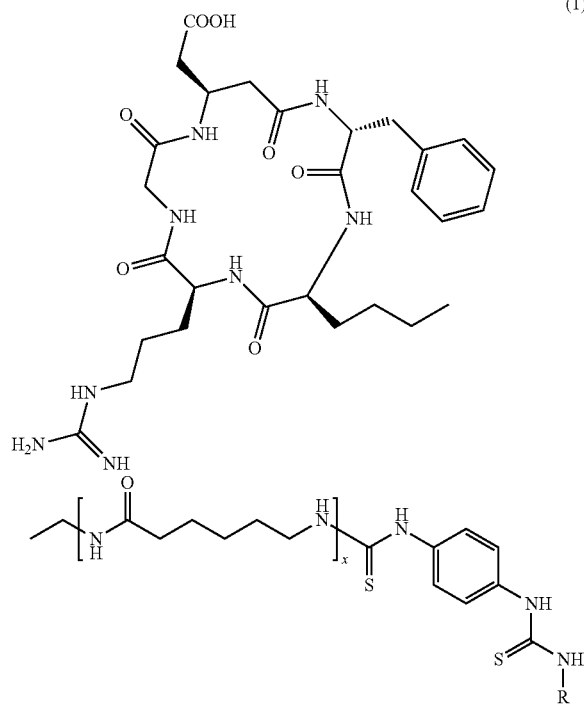

wherein x=0-8 and R is a hydrophobic group.

2. The cRGD peptide derivative according to claim 1, in which the hydrophobic group R is a primary amine R—$NH_2$, which has the same group R, has a logP value greater than −0.2.

3. The cRGD peptide derivative according to claim 2, in which the logP value of the primary amine R—$NH_2$ is greater than 1.9.

4. The cRGD peptide derivative according to claim 1, in which x=4-8.

5. The cRGD peptide derivative according to claim 1, in which R is one or more of a substituted or unsubstituted aliphatic hydrocarbon; a substituted or unsubstituted heteroaliphatic hydrocarbon having at least one heteroatom selected from N, O, S or P; a substituted or unsubstituted aromatic; and a substituted or unsubstituted N-, O-, S- or P-heteroaromatic.

6. The cRGD peptide derivative according to claim 1, in which R is one or more of a chitosan, polylysine, poly(lactide-co-glycolide) (PLGA), and polylactide (PLA).

7. An implant comprising a coating that contains the cyclic Arginine-Glycine-Aspartate (cRGD) peptide derivative having the formula (1):

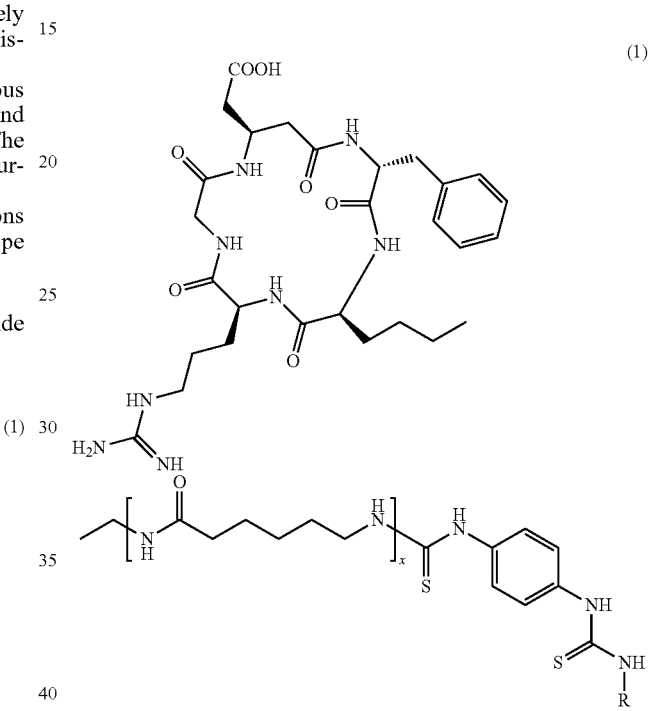

wherein x=0-8 and R is a hydrophobic group.

8. The implant according to claim 7, in which the coating further comprises
    (i) a base comprising of a hydrophobic polymer; and
    (ii) a cover layer that comprises a cRGD peptide derivative; wherein the hydrophobic polymer base comprises poly(lactide-co-glycolide) (PLGA) or polylactide (PLA).

9. The implant according to claim 8, in which the cRGD peptide derivative in the cover layer comprises a hydrophobic polymeric group comprising poly(lactide-co-glycolide) (PLGA) or polylactide (PLA).

10. The implant according to claim 8, in which the cover layer comprises a hydrophobic polymeric group comprising chitosan or polylysine.

11. The implant according to claim 8, in which the hydrophobic polymer comprises an active ingredient.

12. The implant according to claim 7, in which the implant is a stent.

13. The implant according to claim 8, in which the cover layer further comprises a hydrophobic polymeric group comprising: poly(lactide-co-glycolide) (PLGA) or polylactide (PLA).

14. The implant according to claim 10, in which the hydrophobic polymeric group is poly-D-lysine.

15. The implant according to claim 11, in which the active ingredient comprises paclitaxel, sirolimus, or rapamycin.

16. The implant of claim 8 wherein the implant is a medical implant for supporting a hollow vessel, organ or duct, wherein:
the base comprises a base body having a first layer covering the base comprising at least one of poly(lactide-co-glycolide) (PLGA) and polylactide (PLA);
the cRGD peptide derivative is in a cover layer overlying at least a portion of the first layer, wherein x=4-8, R is a hydrophobic group that is selected so that a primary amine R—$NH_2$ has a logP value greater than 1.9, and;
wherein the first layer and coating layer combined have a thickness of between 300 nm to 15 μm.

17. An implant as defined by claim 16 wherein the cover layer comprises one or more of chitosan or polylysine.

18. A method for manufacturing an implant comprising a coating that contains a cRGD peptide derivative having the formula (1):

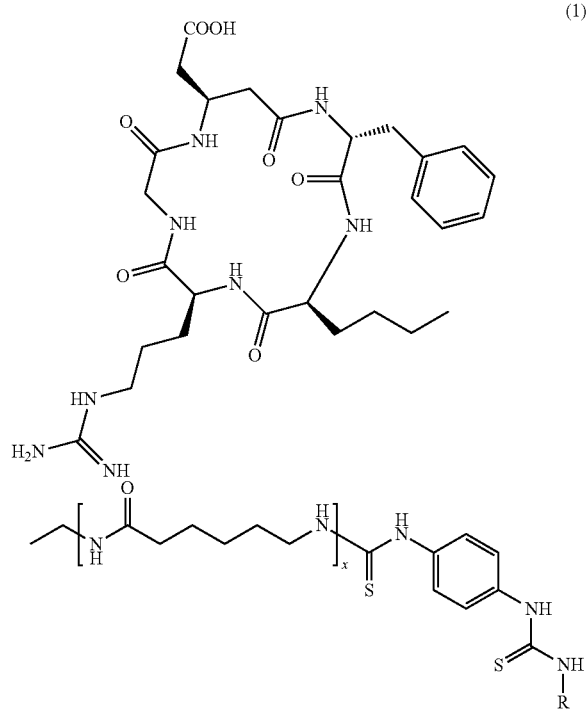

(1)

wherein x=0-8, and R stands for a hydrophobic group, the method comprising the steps:

forming a cRGD peptide derivative by covalent coupling of a primary amine having the formula R—$NH_2$ with the isothiocyanate group of a cRGD peptide derivative having the formula (2)

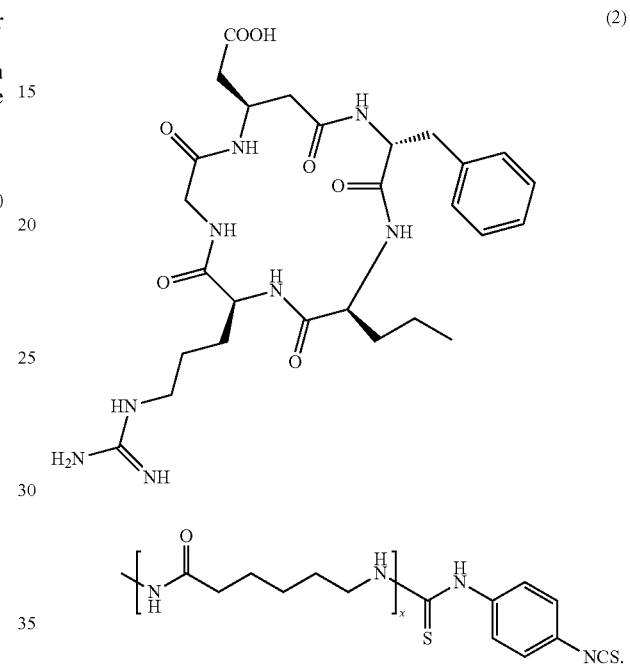

(2)

coating an implant with a coating containing the formed cRGD peptide derivative.

19. The method of claim 18, wherein the step of forming a cRGD peptide derivative by covalent coupling includes use of a primary amine selected from the group consisting of 2-aminoanthracene, 4-heptylaniline, and 1-aminoheptane.

* * * * *